United States Patent [19]

Depreux et al.

[11] Patent Number: 5,332,759

[45] Date of Patent: Jul. 26, 1994

[54] NAPHTHALENE AMIDES AND SULPHONAMIDES, PROCESSES FOR THEIR PREPARATION AND PHARMACEUTICAL COMPOSITIONS CONTAINING THEM

[75] Inventors: Patrick Depreux, Armentieres; Daniel Lesieur, Gondecourt; Habib Abdellaoui, Cuincy; Béatrice Guardiola, Neuilly sur Seine; Gérard Adam, Le Mesnil le Roi; Pierre Renard, Versailles; Bruno Pfeiffer, Eaubonne, all of France

[73] Assignee: Adir et Compagnie, Courbevoie, France

[21] Appl. No.: 9,922

[22] Filed: Jan. 21, 1993

[30] Foreign Application Priority Data

Jan. 22, 1992 [FR] France ................... 92 00608

[51] Int. Cl.$^5$ ................... A61K 31/18; C07C 311/03
[52] U.S. Cl. ................... 514/603; 514/620; 564/86; 564/164
[58] Field of Search ............ 514/603, 620; 564/86, 564/164

[56] References Cited

U.S. PATENT DOCUMENTS

| | | | |
|---|---|---|---|
| 4,900,739 | 2/1990 | Wroel | 514/373 |
| 4,968,679 | 11/1990 | Junge et al. | 514/222.2 |

FOREIGN PATENT DOCUMENTS 0447727 9/1991 European Pat. Off. ........ 564/86

OTHER PUBLICATIONS

McCarthy et al, J. Med. Chem., 28, 1721–1727, 1985.
Alexander et al, J. Org. Chem., 55, 2563–2564, 1990.

*Primary Examiner*—Mukund J. Shah
*Assistant Examiner*—Y. N. Gupta
*Attorney, Agent, or Firm*—Gordon W. Hueschen

[57] ABSTRACT

The invention relates to compounds of the general formula (I):

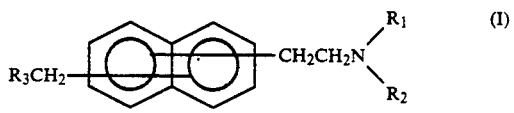

wherein
$R_3$ represents a group

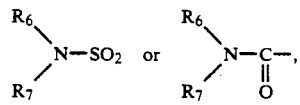

$R_1$, $R_2$, $R_6$, $R_7$ being as defined in the description.

Medicinal product useful in treating a disorder due to vasodilatation of the vascular system.

11 Claims, No Drawings

NAPHTHALENE AMIDES AND SULPHONAMIDES, PROCESSES FOR THEIR PREPARATION AND PHARMACEUTICAL COMPOSITIONS CONTAINING THEM

The present invention relates to new naphthalene amides and sulphonamides, processes for their preparation and pharmaceutical compositions containing them.

Numerous acid derivatives having a naphthalene structure are described in the literature.

With regard to sulphonamides, European Patent EP 397044 describes arylsulphonamides both as antagonists of thromboxane and as inhibitors of thromboxane synthetase.

U.S. Pat. No. 4,900,739 describes sulphonamides having a naphthalene nucleus which are used as intermediates in the synthesis of aldose reductase inhibitors.

The publication J. Org. Chem (1990) 55 (8) pp 2563–4 describes, inter alia, the production of sulphonamides having a naphthalene nucleus.

With regard to amides, Japanese Patent JP 90256655 describes naphthaleneacetamide compounds, antagonists of the glutamate receptor.

The publication J. Med. Chem (1985) 28 (11) pp 1721–7 describes N-alkyl-2-naphthaleneacetamide compounds as intermediates in the synthesis of antidepressants.

The applicants have now discovered new amides and sulphonamides having a naphthalene nucleus which exhibit the property of binding with a high affinity to serotoninergic receptors. That affinity is associated with an extremely high selectivity for 5-HT$_1$ receptors and more especially for 5-HT$_1$D receptors.

The amides and sulphonamides cited in the literature, apart from being structurally very different from the compounds of the invention, are at no point described as exhibiting such an affinity for serotoninergic receptors.

The very good affinity of the compounds of the invention for serotoninergic receptors, associated with their vasoconstrictive properties and their low toxicity, make them valuable for the treatment of pain resulting from vasodilatation of the cranial vascular system, and therefore especially for the treatment of migraines, cephalgia and vascular pains of the face.

The present invention relates more especially to naphthalene compounds of the general formula (I):

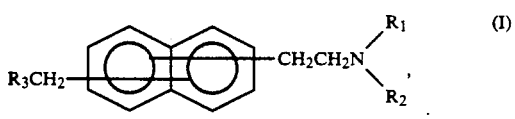

it being possible for each of the two substituents, independently of the other, to be located on either one of the two naphthalene rings, and wherein R$_1$ and R$_2$, which are the same or different, each represents, independently of the other:
  a hydrogen atom,
  a straight-chain or branched alkyl radical having from 1 to 6 carbon atoms,
  a cycloalkyl radical having from 3 to 7 carbon atoms, or a cycloalkyl-(C$_1$-C$_4$)alkyl radical,
  a straight-chain or branched alkenyl radical having from 2 to 6 carbon atoms,
  an optionally substituted aryl radical,
  an optionally substituted aralkyl radical of which the alkyl chain contains from 1 to 3 carbon atoms,
  or, with the nitrogen atom carrying them, together form a ring system selected from:

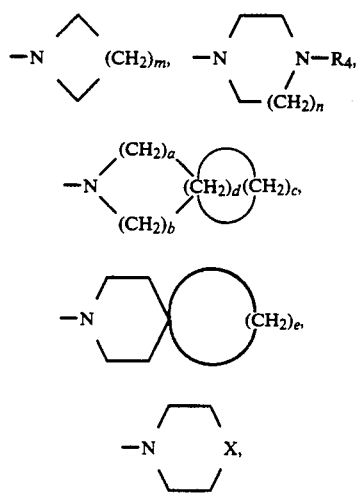

X represents an oxygen or sulphur atom,
m, an integer, may be 0, 1, 2, 3, 4 or 5,
n, an integer, may be 1 or 2,
a and b, integers, may be 0, 1 or 2, with a+b $\neq$ 0,
c and d, integers, may be 0, 1, 2, 3 or 4, with c+d$\neq$0,
e, an integer, may be 4 or 5,
R$_4$ represents:
  a hydrogen atom,
  a straight-chain or branched alkyl radical having from 1 to 6 carbon atoms,
  an optionally substituted aryl radical,
  an optionally substituted aralkyl radical of which the alkyl chain contains from 1 to 3 carbon atoms,
  a

group in which R$_5$ represents a straight-chain or branched alkyl radical having from 1 to 6 carbon atoms or an optionally substituted phenyl or naphthyl radical, R$_3$ represents:

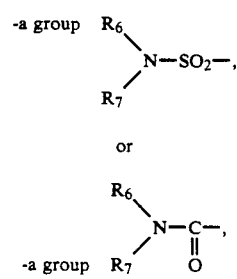

and
R$_6$ and R$_7$, which are the same or different, have the same definition as R$_1$ and R$_2$,
their isomers, enantiomers and diastereoisomers, isolated or in the form of a mixture, and their addition salts with a pharmaceutically acceptable mineral or organic acid;

by "aryl group" there is to be understood a phenyl, naphthyl, pyrimidyl or pyridyl group;

the expressions "optionally substituted aryl" and "optionally substituted aralkyl" indicate that the aromatic nucleus or nuclei may be substituted by one or more hydroxy, halogen, trifluoromethyl, nitro, straight-chain or branched alkyl having from 1 to 6 carbon atoms or straight-chain or branched alkoxy having from 1 to 6 carbon atoms.

The present invention extends also to a process for the preparation of compounds of the general formula (I), which is characterised in that there is used as starting material a naphthalene compound of formula (II):

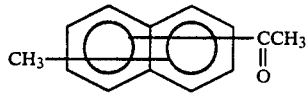
(II)

which is treated with N-bromosuccinimide to obtain the brominated compound of formula (III):

(III)

which may be either:

1) treated with sodium sulphite in an acetone/water mixture to obtain the methanesulphonate of formula (IV):

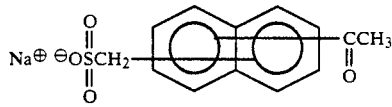
(IV)

which is then treated with phosphorus oxychloride to obtain the sulphonyl chloride of formula (V):

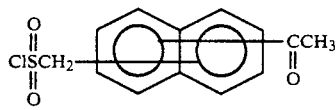
(V)

which is then reacted with an amine of formula (VI):

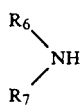
(VI)

wherein $R_6$ and $R_7$ are as defined for compounds of the general formula (I), to obtain the sulphonamide compound of formula (VII):

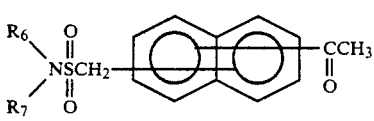
(VII)

wherein $R_6$ and $R_7$ are as defined for compounds of the general formula (I), which is then treated with bromine to obtain the brominated compound of formula (VIII):

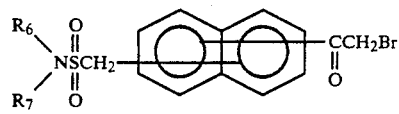
(VIII)

wherein $R_6$ and $R_7$ are as defined for compounds of the general formula (I), which is then reduced by triethylsilane in trifluoroacetic acid to obtain the compound of formula (IX):

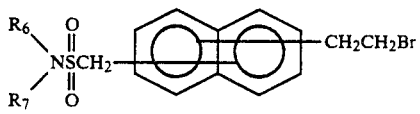
(IX)

wherein $R_6$ and $R_7$ are as defined for compounds of the general formula (I), which is reacted:

either with an amine of formula (X):

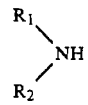
(X)

wherein $R_1$ and $R_2$ are as defined for compounds of the general formula (I), to obtain the compound of formula ($I_{A1}$):

($I_{A1}$)

wherein $R_1$, $R_2$, $R_6$ and $R_7$ are as defined for compounds of the general formula (I), or with potassium phthalimide in DMF to obtain the compound of formula ($XVII_A$):

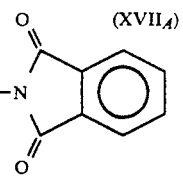
($XVII_A$)

wherein $R_6$ and $R_7$ are as defined for compounds of the general formula (I), which is reacted in alcoholic medium with hydrazine hydrate to obtain the primary amine of formula ($I_{A2}$):

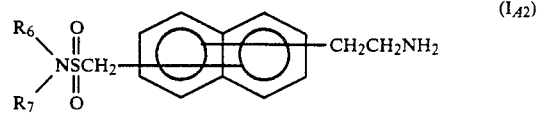
($I_{A2}$)

wherein $R_6$ and $R_7$ are as defined for compounds of the general formula (I), or 2) reacted with an alkali metal cyanide in DMSO or in alcoholic medium to obtain the cyanomethyl compound of formula (XI):

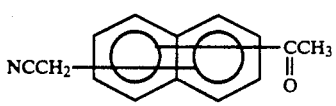
(XI)

which is then hydrolysed, either in aqueous alcoholic medium with an alkali metal hydroxide, or in acidic medium, to obtain the naphthylacetic acid of formula (XII):

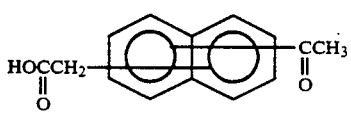
(XII)

which is then treated in conventional manner with thionyl chloride to obtain the acid chloride of formula (XIII):

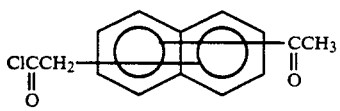
(XIII)

which is then reacted with an amine of formula (VI):

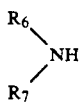
(VI)

wherein $R_6$ and $R_7$ are as defined for compounds of the general formula (I), to obtain the amide compound of formula (XIV):

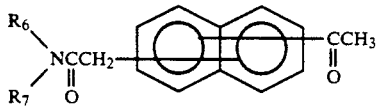
(XIV)

wherein $R_6$ and $R_7$ are as defined for compounds of the general formula (I), which is then treated with bromine to obtain the brominated compound of formula (XV):

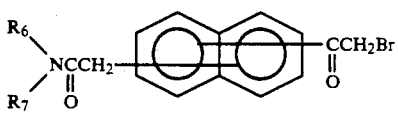
(XV)

wherein $R_6$ and $R_7$ are as defined for compounds of the general formula (I), which is then reduced with triethylsilane in trifluoroacetic acid to obtain the compound of formula (XVI):

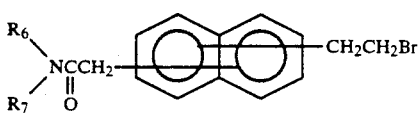
(XVI)

wherein $R_6$ and $R_7$ are as defined for compounds of the general formula (I), which is reacted:
either with an amine of formula (X):

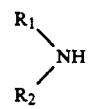
(X)

wherein $R_1$ and $R_2$ are as defined for compounds of the general formula (I), to obtain the compound of formula ($I_{B1}$):

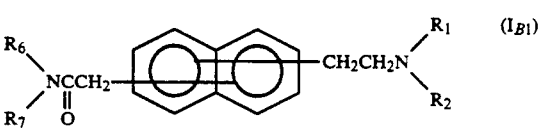
($I_{B1}$)

wherein $R_1$, $R_2$, $R_6$ and $R_7$ are as defined for compounds of the general formula (I), or with potassium phthalimide in DMG to obtain the compound of formula ($XVII_B$):

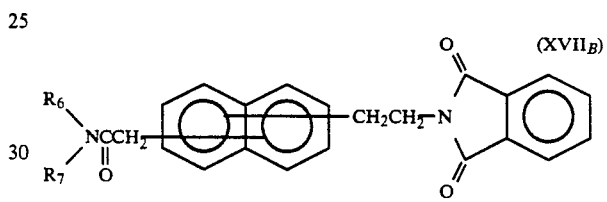
($XVII_B$)

wherein $R_6$ and $R_7$ are as defined for compounds of the general formula (I), which is reacted in alcoholic medium with hydrazine hydrate to obtain the primary amine of formula ($I_{B2}$)

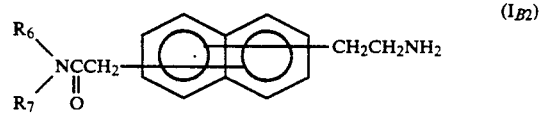
($I_{B2}$)

wherein $R_6$ and $R_7$ are as defined for compounds of the general formula (I), it being understood that the compounds of the general formulae ($I_{A1}$), ($I_{A2}$), ($I_{B1}$) and ($I_{B2}$) represent the totality of the compounds of formula (I) and may, if desired, be converted into salts with a pharmaceutically acceptable acid and, if necessary, separated into their different isomers.

The compounds of the general formula (I) have valuable pharmacological properties.

Studies determining affinity have shown that the compounds of the invention behave like powerful ligands of 5-HT$_1$ receptors and more specially 5-HT$_1$D receptors. That affinity is associated with a high selectivity in relation to other receptors, such as α-adrenergic, dopaminergic, gaba-ergic and histaminergic receptors.

The compounds of the general formula (I) are of low toxicity and have good vasoconstrictive properties which render them valuable in the treatment of pain due to vasodilatation of the vascular system, and thus especially for the treatment of migraines, cephalgia and vascular pains of the face, as well as arterial and veinous circulation disorders.

The present invention relates also to pharmaceutical compositions containing as active ingredient at least one compound of the general formula (I), or an addition salt thereof with a pharmaceutically acceptable acid, alone or in combination with one or more inert, non-toxic excipients or carriers.

Of the pharmaceutical compositions according to the invention there may be mentioned, more especially, those suitable for oral, parenteral or nasal administration, tablets, dragees, sublingual tablets, sachets, paquets, gelatin capsules, glossettes, lozenges, suppositories, creams, ointments, dermic gels etc..

The dosage varies according to the age and weight of the patient, the nature and severity of the disorder and the route of administration, which may be oral, nasal, cutaneous, rectal or parenteral.

Generally, the unit dose ranges from 0.05 to 50 mg from one to three times per day.

The following Examples illustrate the invention but do not limit it in any way.

EXAMPLE 1

2-{1-[2-(Dimethylamino)ethyl]naphth-7-yl}-N-methyl-methanesulphonamide

Step I: 1-Acetyl-7-methylnaphthalene and 6-Acetyl-2methylnaphthalene

Charge 940 g (7.04 mol) of aluminium chloride and 2 liters of chloroform into a reactor under an argon atmosphere. Stir the suspension and then add 552 g (7.04 mol) of acetyl chloride followed by a solution of 1 kg (7.04 mol) of 2-methylnaphthalene in 3.3 liters of chloroform. Stir the reaction mixture for 1 hour at room temperature, and then hydrolyse it by pouring it onto a mixture of ice-water. Extract with methylene chloride and then concentrate to dryness under partial pressure.

The resulting crude oil is distilled in vacuo.

1-acetyl-7-methylnaphthalene is obtained in a yield of 13%, b.p. 0.06 mm Hg: 114°–115° C.

At the same time, 6-acetyl-2-methylnaphthalene is isolated in a yield of 28%, b.p. 0.06 mm Hg: 118°–120° C.

Step II: 1-Acetyl-7-bromomethylnaphthalene

Charge 100 g (0.54 mol) of 1-acetyl-7-methylnaphthalene, 97 g (0.54 mol) of N-bromosuccinimide, 14 g of benzoyl peroxide and 1.4 liters of carbon tetrachloride into a reactor under a nitrogen atmosphere.

Heat at reflux for one hour, then cool and remove insoluble material by filtration.

Wash the organic phase with water and then concentrate to dryness.

The crude product, obtained in a quasi-quantitative yield, is then purified by chromatography twice on a silica column.

Eluant of the first column: heptane 80%, ethyl acetate 20%.

Eluant of the second column: toluene 70%, cyclohexane 30%.

Melting point: 68° C.

Infrared (KBr disc): 1660 cm$^{-1}$ $\nu$ C=O 1360 cm

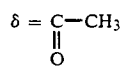

840, 760 and 725 cm$^{-1}$ δCH

NMR (CDCl$_3$, TMS):

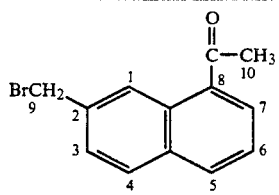

| Proton No. | 1 | 3 | 4 | 5 | 6 | 7 | 9 | 10 |
|---|---|---|---|---|---|---|---|---|
| δ (ppm) | 8.79 | 7.55 | 7.83 | 7.94 | 7.48 | 7.94 | 4.65 | 2.72 |

Step III: Sodium 2-(1-Acetylnaphth-7-yl)methanesulphonate

Dissolve 20 g (0.076 mol) of 1-acetyl-7-bromomethylnaphthalene in 70 cm$^3$ of acetone, then add, with sti a solution of 9.57 g (0.076 mol) of sodium sulphite in 130 cm$^3$ of water.

Heat the reaction mixture at reflux for two hours, then cool, filter, and concentrate the filtrate to dryness under partial pressure.

Recrystallise the resulting solid residue from ethanol at 95°.

In that manner 18.49 g (85%) of sodium 2-(1-acetyl-naphth-7-yl)methanesulphonate are obtained.

Melting point: >260° C.

Microanalysis: calculated C(54.53), H(3.87). found C(54.26), H(3.99).

Infrared (KBr disc): 3040–2920 cm$^{-1}$ $\nu$ CH (alkyl), 1660 cm$^{-1}$ $\nu$ C=O, 1590 and 1560 cm$^{-1}$ $\nu$ C=C, 1192–1175 cm$^{-1}$ $\nu$ SO$_2$, 1065–1050 cm$^{-1}$ $\nu$ SO$_2$.

NMR (DMSO, d$_6$) δ (ppm):

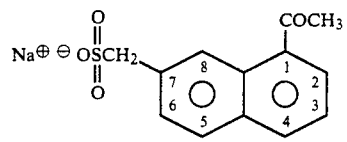

2.74 (s, 3H) CH$_3$, 3.92 (s, 2H) CH$_2$, 7.44–8.13 (unresolved peaks, 5H) H$_2$, H$_3$, H$_4$, H$_5$, H$_6$ 8.48 (1H) H$_8$.

Step IV: 2-(1-Acetylnaphth-7-yl)methanesulphonic Acid Chloride

Charge into a flask under an argon atmosphere 11.44 g (0.04 mol) of sodium 2-(1-acetylnaphth-7-yl)methanesulphonate, 14.6 cm$^3$ (0.15 mol) of phosphorus oxy 20 cm$^3$ of sulpholane and 20 cm$^3$ of anhydrous acetonitrile.

Heat the reaction mixture, with stirring, for 40 minutes at 70° C.

After cooling, hydrolyse the reaction mixture by pouring it onto ice, isolate the resulting precipitate by means of filtration, wash with water and dry.

In that manner 9.61 g (85%) of 2-(1-acetylnaphth-7-yl)methanesulphonic acid chloride are obtained.

Melting point: 129°–130° C.

Infrared (KBr disc): 3090–2600 cm$^{-1}$ $\nu$ CH (alkyl), 1660 cm$^{-1}$ $\nu$ C=O, 1590 and 1560 cm$^{-1}$ $\nu$ C=C (aromatic), 1360 and 1155 cm$^{-1}$ $\nu$ SO$_2$.

NMR (DMSO, d$_6$) δ (ppm):

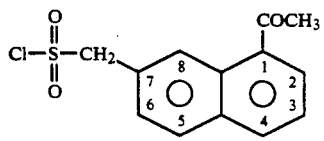

2.75 (s, 3H) CH₃, 5.06 (s, 2H) CH₂, 7.50–8.08 (unresolved peaks, 5H) H₂, H₃, H₄, H₅, H₆ 9.00 (1H) H₈.

Step V:
2-(1-Acetylnaphth-7-yl)-N-methyl-methanesulphonamide

Dissolve 10.5 g (0.037 mol) of 2-(1-acetylnaphth-7-yl)methanesulphonic acid chloride in 200 cm³ of ethyl acetate. Cool to 0° C. and add dropwise 9 cm³ (0.11 mol) of an aqueous 40% methylamine solution.

Stir for 30 minutes at room temperature, wash the organic phase with water, concentrate it to a third of its initial volume and isolate the resulting precipitate by means of filtration.

The crude product is recrystallised from ethanol at 95°.

In that manner 7.9 g (77%) of 2-(1-acetylnaphth-7-yl)-N-methyl-methanesulphonamide are obtained.

Melting point: 127°–129° C.

Microanalysis: calculated C(60.63), H(5.45), N(5.05). found C(60.53), H(5.15), N(5.22).

Infrared (KBr disc): 3240 cm⁻¹ ν NH (sulphonamide), 3040–2920 cm⁻¹ ν CH (alkyl), 1660 cm⁻¹ ν C=O,

1590 and 1560 cm⁻¹ ν C=C (aromatic), 1310 cm⁻¹ ν SO₂.

NMR (DMSO, d₆) δ (ppm):

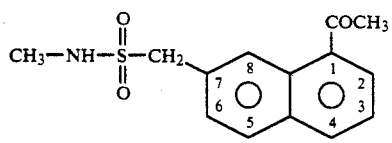

2.61 (3H) CH₃NH 2.75 (s, 3H) CH₃C
||
O 4.55 (s, 2H) CH₂SO₂, 6.96 (m, 1H) NH (exchangeable in D₂O), 7.50–8.70 (unresolved peaks, 5H) H₂, H₃, H₄, H₅, H₆ 8.63 (1H) H₈.

Step VI:
2-(1-Bromoacetylnaphth-7-yl)-N-methyl-methanesulphonamide

Dissolve 6.3 g (0.022 mol) of 2-(1-acetylnaphth-7-yl)-N-methyl-methanesulphonamide at 60° C. in 100 cm³ of acetic acid.

Add dropwise 1.17 cm³ (0.022 mol) of bromine in 80 cm³ of acetic acid.

When the addition is complete, continue stirring for 2 hours at 60° C.

After cooling, pour the reaction mixture into 150 cm³ of water, isolate the resulting precipitate by means of filtration, wash with a minimum of acetonitrile and recrystallise from acetonitrile.

In that manner 6.58 g (84%) of 2-(1-bromoacetylnaphth-7-yl)-N-methyl-methanesulphonamide are obtained.

Melting point: 159°–161° C.

Microanalysis: calculated C(47.19), H(3.96), N(3.93). found C(47.16), H(3.85), N(3.90).

Infrared (KBr disc): 3260 cm⁻¹ ν NH 1675–1655 cm⁻¹ ν C=O, 1590 and 1565 cm⁻¹ ν C=C (aromatic).

NMR (DMSO, d₆) δ (ppm):

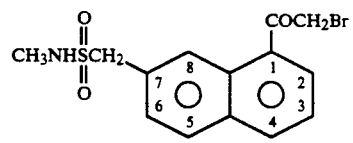

2.61 (d, 3H) CH₃NH (J CH₃NH=4.6 Hz, no coupling in D₂O), 4.50 (s, 2H) CH₂SO₂, 5.07 (s, 2H) CH₂Br, 6.96 (q, 1H) NH (J NHCH₃=4.6 Hz, no coupling in D₂O), 8.00–8.80 (unresolved peaks, 5H) H₂, H₃, H₄, H₅, H₆ 8.50 (1H) H₈.

Step VII:
2-[1-(2-Bromoethyl)naphth-7-yl]-N-methyl-methanesulphonamide

Dissolve 10.4 g (0.029 mol) of 2-(1-bromoacetylnaphth-7-yl)-methyl-methanesulphonamide in 16 cm³ of trifluoroacetic acid under an argon atmosphere, then add dropwise 10.26 cm³ (0.064 mol) of triethylsilane.

Stir for 72 hours at room temperature, then pour the reaction mixture into 360 cm³ of iced water.

Isolate the resulting precipitate by means of filtration, wash it with water and then, after drying, recrystallise it from ethanol at 95°.

In that manner 7.94 g (80%) of 2-[1-(2-bromoethyl)-naphth-7-yl]-N-methyl-methanesulphonamide are obtained.

Melting point: 86°–88° C.

Microanalysis: calculated C(49.12), H(4.71), N(4.09). found C(49.23), H(4.69), N(3.97).

Infrared (KBr disc): 3270 cm⁻¹ ν NH, 1590 cm⁻¹ ν C=C (aromatic), 1310 cm⁻¹ ν SO₂ (sulphonamide).

NMR (DMSO, d₆) δ (ppm):

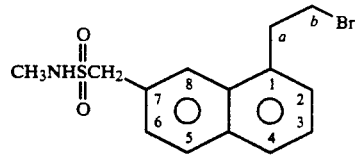

2.61 (d, 3H) CH₃NH (J CH₃NH=5.7 Hz, no coupling in D₂O) 3.50–4.00 (unresolved peaks, 4H) CH₂a and CH₂b 4.57 (s, 2H) CH₂SO₂ 7.00 (q, 1H) NHCH₃ (J NHCH₃=5.7 Hz, no coupling in D₂O) 7.50–8.08 (unresolved peaks, 6H) H₂, H₃, H₄, H₅, H₆, H₈.

Step VIII:
2-{1-[2-(Dimethylamino)ethyl]naphth7-yl}-N-methyl-methanesulphonamide Introduce a solution of 2-[1-(2-bromoethyl)naphth-7-yl]-N-methyl-methanesulphonamide in 30 cm³ of ethanol into an autoclave at 95°.

Add 7.4 cm³ (0.096 mol) of an aqueous 40% dimethylamine solution and heat for 8 hours at 80° C.

After cooling, concentrate to dryness, take up the residue in 30 cm³ of water, render acidic, wash the aqueous phase with ether, render alkaline, isolate the resulting precipitate by means of filtration, wash it with water and then, after drying, recrystallise it from absolute ethanol.

In that manner 1.18 g (40%) of 2-{1-[2-(dimethylamino)ethyl]naphth-7-yl}-N-methyl-methanesulphonamide is obtained.

Melting point: 149°–150° C.

Microanalysis: calculated C(62.71), H(7.23), N(9.14). found C(62.89), H(7.33), N(9.12).

Infrared (KBr disc): 3080–3040 cm⁻¹ ν NH, 2970–2760 cm⁻¹ ν CH, 1590 cm⁻¹ ν C=C (aromatic), 1310 cm⁻¹ ν SO₂.

NMR (DMSO, d₆) δ (ppm):

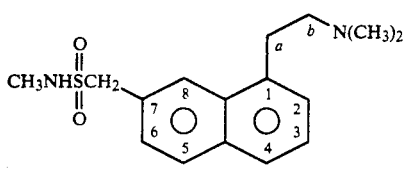

2.26 (d, 6H) N(CH₃)₂, 2.35–2.50 (m, 2H) CH₂b, 2.60 (d, 3H) CH₃NH (J CH₃NH=4.2 Hz, no coupling in D₂O), 3.10 (m, 2H) CH₂a, 4.54 (s, 2H) CH₂SO₂, 6.94 (q, 1H) NHCH₃ (J NHCH₃=4.2 Hz, no coupling in D₂), 7.38–8.05 (unresolved peaks, 6H) H₂, H₃, H₄, H₅, H₆, H₈.

EXAMPLE 2

2-[1-(2-Aminoethyl)naphth-7-yl]-N-methyl-methanesulphonamide

Step I:
2-[1-(2-Phthalimidoethyl)naphth-7-yl]-N-methyl-methanesulphonamide

Dissolve 3 g (8.7 mmol) of 2-[1-(2-bromoethyl)-naphth-7-yl]-N-methyl-methanesulphonamide (Example 1 Step VII) in 20 cm³ of dimethylformamide, then add 1.61 g (8.7 mmol) of potassium phthalimide and heat at reflux for 48 hours.

After cooling, pour the reaction mixture into 150 cm³ of water, isolate the product that precipitates by means of filtration and then, after drying, recrystallise it from dimethylformamide.

In that manner 1.77 g (50%) of 2-[1-(2-phthalimidoethyl)naphth-7-yl]-N-methyl-methanesulphonamide are obtained.

Melting point: 248°–251° C.

Microanalysis: calculated C(64.68), H(4.93), N(6.85). found C(64.33), H(5.01), N(6.99).

Infrared (KBr disc): 3310 cm⁻¹ ν NH, 3000–2900 cm⁻¹ ν CH, 1760–1700 cm⁻¹ ν C=O (phthalimide).

NMR (DMSO, d₆) δ (ppm):

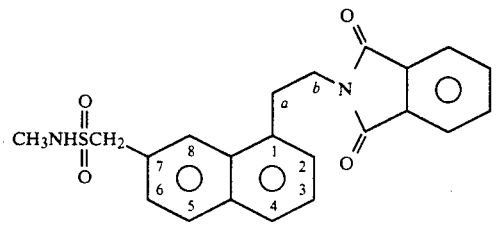

2.60 (d, 3H) CH₃NH (J CH₃NH=4.2 Hz, no coupling in D₂O), 4.00 (m, 4H) CH₂a, CH₂b, 4.54 (s, 2H) CH₂SO₂, 7.00 (q, 1H) NHCH₃ (J NHCH₃=4.2 Hz, no coupling in D₂O), 8.00–7.32 (unresolved peaks, 9H) H₂, H₃, H₄, H₅, H₆+phthalimide, 8.30 (signal, 1H) H₈.

Step II:
2-[1-(2-Aminoethyl)naphth-7-yl]-N-methyl-methanesulphonamide

Suspend 3 g (7.3 mmol) of 2-[1-(2-phthalimidoethyl)-naphth-7-yl]-N-methyl-methanesulphonamide in 80 cm³ of alcohol at 95°, then heat at reflux and add dropwise 8 cm³ of 98% hydrazine hydrate until the starting material has dissolved completely.

Continue heating for two hours and then, after cooling, remove the phthalic hydrazide precipitate by means of filtration.

Concentrate to dryness the filtrate, take up the residue in 50 cm³ of absolute alcohol, and then bubble with hydrochloric acid until precipitation of the amine hydrochloride, which is isolated by filtration, dried, and then recrystallised from absolute ethanol.

In that manner 0.92 g (40%) of 2-[1-(2-aminoethyl)-naphth-7-yl]-N-methyl-methanesulphonamide hydrochloride are obtained.

Melting point: 233°–237° C.

Microanalysis: calculated C(53.40), H(6.08), N(8.89). found C(54.14), H(6.20), N(8.86).

Infrared (KBr disc): 3300–2500 cm³¹ ¹ ν NH+ (hydrochloride), 1590 cm⁻¹ ν C=C (aromatic), 1310 cm⁻¹ ν SO₂.

NMR (DMSO, d₆) δ (ppm):

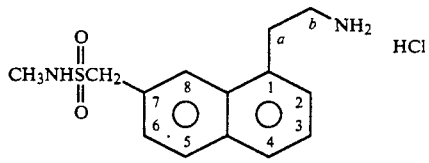

2.63 (d, 3H) CH₃NH (J CH₃NH=4.61 Hz, no coupling in D₂O), 3.25 (m, 4H) CH₂a, CH₂b, 4.57 (s, 2H) CH₂SO₂, 7.00 (q, 1H) NHCH₃ (J NHCH₃=4.61 Hz, no coupling in D₂O), 7.46–8.00 (unresolved peaks, 6H) H₂, H₃, H₄, H₅, H₆, H₈ 8.25 (signal, 2H) NH+ (disappears in D₂O).

EXAMPLE 3

2-[1-(2-Morpholinoethyl)naphth-7-yl]-N-methyl-methanesulphonamide Hydrochloride

Dissolve 3.42 g (0.01 mol) of 2-[1-(2-bromoethyl)-naphth-7-yl]-N-methyl-methanesulphonamide in 40 cm³ of acetone.

Add dropwise 1.74 g (0.02 mol) of morpholine and heat at reflux for 24 hours.

After cooling, concentrate the reaction mixture to dryness, take up the residue in water, render acidic, wash with ethyl acetate, render alkaline and extract with ether.

Wash the ethereal phase with water, dry, and then bubble through it a stream of gaseous hydrochloric acid.

Isolate the resulting precipitate by means of filtration and recrystallise it from methanol.

In that manner 1.31 g (34%) of 2-[1-(2-morpholinoethyl)naphth-7-yl]-N-methyl-methanesulphonamide hydrochloride are obtained.

Melting point: 216°–218° C.

Microanalysis: calculated C(56.16), H(6.54), N(7.27). found C(56.01), H(6.62), N(7.36).

Infrared (KBr disc): 3010 cm$^{-1}$ $\nu$ NH (sulphonamide), 2900 cm$^{-1}$ $\nu$ CH (alkyl), 2800–2520 cm$^{-1}$ $\nu$ NH (amine), 1590 cm$^{-1}$ $\nu$ C=C (aromatic).

NMR (DMSO, d$_6$) $\delta$ (ppm):

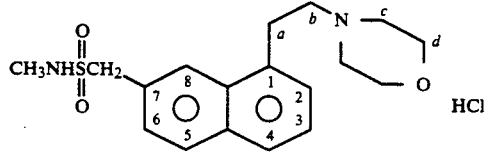

2.64 (d, 3H) CH$_3$NH (J CH$_3$NH=4.3 Hz, no coupling in D$_2$O), 3.18–4.00 (unresolved peaks, 12H) CH$_2$a, CH$_2$b, CH$_2$c, CH$_2$d, 4.59 (s, 2H) CH$_2$SO$_2$, 7.00 (q, 1H) NHCH$_3$ (J NHCH$_3$=4.3 Hz, no coupling in D$_2$O), 7.50–8.00 (unresolved peaks, 5H) H$_2$, H$_3$, H$_4$, H$_5$, H$_6$, 8.40 (1H) H$_8$, 11.89 (1H) NH$^+$ (exchangeable in D$_2$O).

EXAMPLE 4

2-{1-[2-(3-Azabicyclo[3.3.0]oct-3-yl)ethyl)naphth-7-yl]-N-methyl-methanesulphonamide By proceeding as in Example 3, but replacing the morpholine with 3-azabicyclo[3.3.0]octane, 2-{1-[2-(3-azabicyclo[3.3.0]oct-3-yl)ethyl]naphth-7-yl}-N-methyl-methanesulphonamide is obtained in a yield of 32%.

Melting point: 130°–132° C.

Microanalysis: calculated C(67.70), H(7.57), N(7.52). found C(67.78), H(7.69), N(7.38).

Infrared (KBr disc): 3040–3060 cm$^{-1}$ $\nu$ NH (sulphonamide), 2780–2940 cm$^{-1}$ $\nu$ CH, 1320 cm$^{-1}$ $\nu$ SO$_2$.

NMR (DMSO, d$_6$) $\delta$ (ppm):

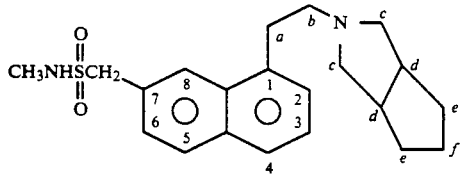

1.50 (m, 6H) CH$_2$e, CH$_2$f, 2.09–2.75 (unresolved peaks, 11H) CH$_2$b, CH$_2$c, CH$_2$d and CH$_3$N, 3.32 (m, 2H) CH$_2$a, 4.53 (s, 2H) CH$_2$SO$_2$, 7.00 (m, 1H) NHCH$_3$ (exchangeable in D$_2$O), 7.38–8.09 (unresolved peaks, 6H) H$_2$, H$_3$, H$_4$, H$_5$, H$_6$, H$_8$.

EXAMPLE 5

2-[1-(2-Piperidinoethyl)naphth-7-yl]-N-methyl-methanesulphonamide Hydrochloride

By proceeding as in Example 3, but replacing the morpholine with piperidine, 2-[1-(2-piperidinoethyl)]-naphth-7-yl)-N-methyl-methanesulphonamide hydrochloride is obtained.

Melting point: 202°–204° C.

Microanalysis: calculated C(59.58), H(7.10), N(7.31). found C(59.43), H(7.34), N(7.35).

Infrared (KBr disc): 3000–3020 cm$^{-1}$ $\nu$ NH (sulphonamide), 2900 cm$^{-1}$ $\nu$ CH (alkyl), 2500–2800 cm$^{-1}$ $\nu$ NH (hydrochloride), 1595 cm$^{-1}$ $\nu$ C=C (aromatic).

NMR (DMSO, d$_6$) $\delta$ (ppm):

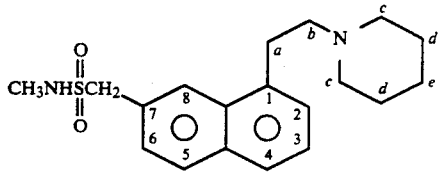

1.83 (unresolved peaks, 6H) CH$_2$d, CH$_2$e, 2.67 (d, 3H) CH$_3$NH (J CH$_3$NH=4.3 Hz, no coupling in D$_2$O) 3.00–3.72 (unresolved peaks, 8H) CH$_2$a, CH$_2$b, CH$_2$c, 4.59 (s, 2H) CH$_2$SO$_2$, 7.00 (q, 1H) NHCH$_3$ (J NHCH$_3$=4.3 Hz, no coupling in D$_2$O), 7.50–8.00 (unresolved peaks, 5H) H$_2$, H$_3$, H$_4$, H$_5$, H$_6$ 8.37 (1H) H$_8$, 11.00 (1H) NH$^+$ in D$_2$O).

EXAMPLE 6

2-{1-[2-(4-Meta-trifluoromethylphenylpiperazin-1-yl)ethyl]naphth-7-yl}-N-methyl-methanesulphonamide Hydrochloride Add 2.02 g (0.007 mol) of meta-trifluoromethylphenylpiperazine hydrochloride, then 2 cm$^3$ (0.014 mol) of triethylamine, to a solution of 2.5 g (0.007 mol) of 2-[1-(2-bromoethyl)naphth-7-yl]-N-methyl-methanesulphonamide in 40 cm$^3$ of acetone.

Heat at reflux for 48 hours, then concentrate to dryness, take up the residue in water, render acidic, wash with ethyl acetate, render alkaline, extract with ethyl acetate and then concentrate to dryness after drying.

Take up the residue in absolute ethanol, bubble through it gaseous hydrochloric acid, isolate the hydrochloride by means of filtration and recrystallise it from acetonitrile.

In that manner 0.81 g (22%) of 2-{1-[2-(4-metatrifluoromethylphenylpiperazin-1-yl)ethyl]naphth-7-yl-}-N-methyl-methanesulphonamide hydrochloride is obtained.

Melting point: 234°–236 ° C.

Microanalysis: calculated C(56.86), H(5.53), N(7.95). found C(56.84), H(5.10), N(7.96).

Infrared (KBr disc): 3090 cm$^{-1}$ $\nu$ NH (sulphonamide), 2929–2820 cm$^{-1}$ $\nu$ CH (alkyl), 2680–2400 cm$^{-1}$ $\nu$ NH (hydrochloride), 1610–1590 cm$^{-1}$ $\nu$ C=C (aromatic), 1320 cm$^{-1}$ $\nu$ SO$_2$.

NMR (DMSO, d$_6$) $\delta$ (ppm):

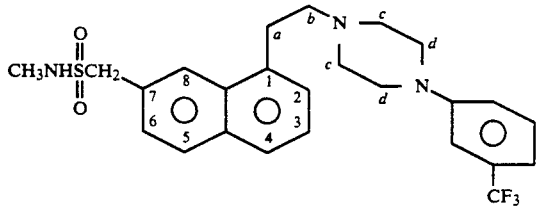

2.64 (d, 3H) CH$_3$NH (J CH$_3$NH=4.3 Hz, no coupling in D$_2$O) 3.24–4.10 (unresolved peaks, 12H) CH$_{2a}$, CH$_{2b}$, CH$_{2c}$, CH$_{2d}$, 4.59 (s, 2H) CH$_2$SO$_2$, 7.00 (q, 1H) NHCH$_3$ (J NHCH$_3$=4.3 Hz, no coupling in D$_2$O), 7.13–8.05 (unresolved peaks, 9H) H$_2$, H$_3$, H$_4$, H$_5$, H$_6$, aromatic protons, 8.37 (1H) H₈, 11.5 (m, 1H) NH⁺ (exchangeable in D₂O).

EXAMPLES 7 to 13

By proceeding as in Example 6, but replacing the 1-(meta-trifluoromethylphenyl)piperazine with:

1-(naphth-1-yl)piperazine, there is obtained:

Example 7: 2-{1-[2-(4-(Naphth-1-yl)piperazin-1-yl)ethyl]naphth-7-yl}-N-methyl-methanesulphonamide Hydrochloride 1-(pyrid-2-yl)piperazine, there is obtained:

Example 8: 2-{1-[2-(4-(Pyrid-2-yl)piperazin-1-yl)ethyl]naphth-7-yl}-N-methyl-methanesulphonamide Hydrochloride 1-(pyrimid-2-yl)piperazine, there is obtained:

Example 9: 2-{1-[2-(4-(Pyrimid-2-yl)piperazin-1-yl)ethyl]naphth-7-yl}-N-methyl-methanesulphonamide Hydrochloride 1-benzylpiperazine, there is obtained:

Example 10: 2-{1-[2-(4-Benzylpiperazin-1-yl)ethyl]naphth-7-yl}-N-methanesulphonamide Hydrochloride 1-methylpiperazine, there is obtained:

Example 11: 2-{1-[2-(4-Methylpiperazin-1-yl)ethyl]naphth-7-yl}-N-methyl-methanesulphonamide Hydrochloride 3-azaspiro[5.5]undecane, there is obtained:

Example 12: 2-{1-[2-(3-Azaspiro[5.5]undecan-3-yl)ethyl]naphth-7-yl)-N-methyl-methanesulphonamide Hydrochloride 3-azabicyclo[3.2.2]nonane, there is obtained:

Example 13: 2-{1-[2-(3-Azabicyclo[3.2.2]nonan-3-yl)ethyl]naphth-7-yl}-N-methyl-methanesulphonamide Hydrochloride

EXAMPLES 14 to 21

By proceeding as in Example 3, but replacing the morpholine with:

pyrrolidine, there is obtained:

Example 14: 2-[1-(2-Pyrrolidinoethyl)naphth-7-yl]-N-methyl-methanesulphonamide Hydrochloride thiomorpholine, there is obtained:

Example 15: 2-[1-(2-Thiomorpholinoethyl)naphth-7-yl]-N-methyl-methanesulphonamide Hydrochloride hexamethyleneimine, there is obtained:

Example 16: 2-[1-(2-Hexamethyleneiminoethyl)naphth-7-yl]-N-methyl-methanesulphonamide Hydrochloride heptamethyleneimine there is obtained:

Example 17: 2-[1-(2-Heptamethyleneiminoethyl)-naphth-7yl]-N-methyl-methanesulphonamide Hydrochloride N,N-dipropylamine, there is obtained:

Example 18: 2-{1-[2-(N,N-Dipropylamino)ethyl]-naphth-7-yl}-N-methyl-methanesulphonamide Hydrochloride Melting point: 177°-180° C.

N-benzylmethylamine, there is obtained:

Example 19: 2-{1-[2-(N-Benzyl-N-methylamino)ethyl]-naphth-7-yl}-N-methyl-methanesulphonamide Hydrochloride Melting point: 187°-189° C.

N-methylaniline, there is obtained:

Example 20: 2-{1-[2-(N-Methyl-N-phenylamino)ethyl]-naphth-7-yl}-N-methyl-methanesulphonamide Hydrochloride cyclohexylamine, there is obtained:

Example 21: 2-{1-[2-(N-Cyclohexylamino)ethyl]-naphth-7-yl}-N-methyl-methanesulphonamide Hydrochloride

EXAMPLES 22 to 23

By proceeding as in Example 1, Step VIII, but replacing dimethylamine with:

methylamine in 40% strength aqueous solution, there is obtained:

Example 22: 2-{1-[2-(N-Methylamino)ethyl]naphth-7-yl}-N-methyl-methanesulphonamide Melting point: 145°-148° C.

N-methyl-N-ethylamine, there is obtained:

Example 23: 2-{1-[2-(N-Methyl-N-ethylamino)ethyl]-naphth-7-yl}-N-methyl-methanesulphonamide Example 24: 2-{1-[2-(Dimethylamino)ethyl]-7-yl}-N-benzyl-methanesulphonamide By proceeding as in Example 1, but replacing the 2-[1-(2-bromoethyl)naphth-7-yl]-N-methyl-methanesulphonamide in Step VIII with 2-[1-(2-bromoethyl)-naphth-7-yl]-N-benzyl-methanesulphonamide, 2-{1-[2-(dimethylamino)ethyl]naphth-7-yl}-N-benzyl-methanesulphonamide in the hydrochloride form is obtained in a yield of 55%.

Melting point: 151°-154° C. (hydrochloride)

Infrared (KBr disc): 3120–3020 cm⁻¹ ν NH (sulphonamide), 2960–2800 cm⁻¹ ν CH, 2700–2400 cm⁻¹ ν NH⁺ (hydrochloride), 1590 cm⁻¹ ν C=C (aromatic), 1310 cm⁻¹ ν SO₂ (sulphonamide).

NMR (DMSO, d₆) δ (ppm):

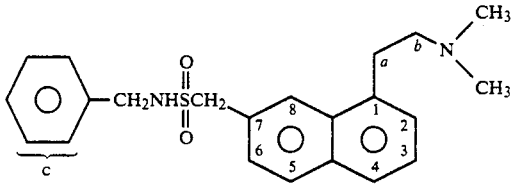

2.85 (s, 6H) N(CH₃)₂, 3.30 (m, 2H) Hb, 3.50 (m, 2H) Ha, 4.17 (d, 2H) CH₂NH, 4.60 (s, 2H) CH₂SO₂, 7.30 (unresolved peaks, 5H) Hc, 7.50–8.00 (unresolved peaks, 6H) H₂, H₃, H₄, H₅, H₆ and NHCH₃ (disappears in D₂O), 8.28 (signal, 1H) H₈.

The 2-[1-(2-bromoethyl)naphth-7-yl]-N-benzyl-methanesulphonamide is prepared in two steps from 2-(1-acetylnaphth-7-yl)-N-benzyl-methanesulphonamide as in Example 1.

2-(1-acetylnaphth-7-yl)-N-benzyl-methanesulphonamide

Melting point: 131° C.

Infrared (KBr disc): 3300–3220 cm⁻¹ ν NH, 1660–1640 cm⁻¹ ν C=O,

NMR (DMSO, d₆) δ (ppm):

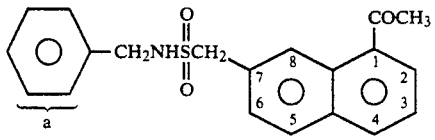

2.75 (s, 3H) CH₃, 4.25 (m, 3H) CH₂— NH, 4.45 (s, 2H) CH₂SO₂, 7.3–8.06 (m, 10H) H₂, H₃, H₄, H₅, H₆, Ha, 8.7 (s, 1H) H₈.

EXAMPLE 25

1-[2-(Dimethylamino)ethyl]-7-morpholinosulphonyl-methylnaphthalene

By proceeding as in Example 19, but starting from 1-acetyl-7-morpholinosulphonylmethylnaphthalene, 1-[2-(dimethylamino)ethyl]-7-morpholinosulphonylmethylnaphthalene is obtained in a yield of 35%.

Melting point: 114°–117° C.

Infrared (KBr disk): 3960–2820 cm$^{-1}$ $\nu$ CH alkyl, 1590 cm$^{-1}$ $\nu$ C=C (aromatic), 1340–1320 cm$^{-1}$ $\nu$ $SO_2$ (sulphonamide).

NMR (CDCl$_3$) δ (ppm):

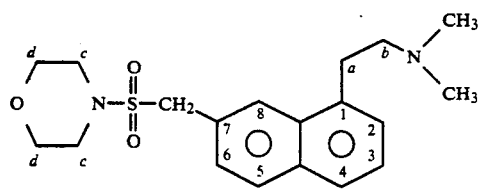

2.42 (s, 6H) —N(CH$_3$)$_2$, 2.74 (m, 2H) Hb, 3.14 (m, 2H) Hc, 3.29 (m, 2H) Ha, 3.59 (m, 2H) Hd, 4.46 (s, 2H) CH$_2$SO$_2$, 7.40–7.96 (unresolved peaks, 5H) H$_2$, H$_3$, H$_4$, H$_5$, H$_6$, 8.13 (signal, 1H) H$_8$.

1-acetyl-7-(morpholinosulphonylmethyl)naphthalene

Melting point: 162° C. (ethyl acetate)

Infrared (KBr disk): 3000–2800 cm$^{-1}$ $\nu$ CH, 1670–1660 cm$^{-1}$ $\nu$ C=O.

NMR (CDCl$_3$) δ (ppm):

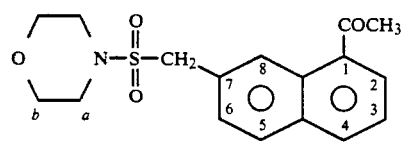

2.80 (s, 3H) CH$_3$, 3.15 (m, 4H) Ha, 3.60 (m, 4H) Hb, 4.45 (s, 2H) CH$_2$, 7.6–8.10 (m, 5H), 8.90 (s, 1H).

EXAMPLES 26 to 28

By proceeding as in Example 24, but replacing 2-[1-(2-bromoethyl)naphth-7-yl]-N-benzyl-methanesulphonamide with:

2-[1-(2-bromoethyl)naphth-7-yl]-N,N-dimethyl-methanesulphonamide, there is obtained:

Example 26: 2-{1-[2-(Dimethylamino)ethyl]naphth-7-yl}-N,N-dimethyl-methanesulphonamide Melting point: 110°–113° C.

Infrared (KBr disk): 2980–2720 cm$^{-1}$ $\nu$ CH alkyl, 1590 cm$^{-1}$ $\nu$ C=C (aromatic), 1330 cm$^{-1}$ $\nu$ SO$_2$ (sulphonamide).

2-[1-(2-bromoethyl)naphth-7-yl]-N-cyclopentylmethanesulphonamide, there is obtained:

Example 27: 2-{1-[2-(Dimethylamino)ethyl]naphth-7-yl}-N-cyclopentyl-methanesulphonamide 2-[1-(2-bromoethyl)naphth-7-yl]-N-tetramethylenemethanesulphonamide, there is obtained:

Example 28: 2-{1-[2-(Dimethylamino)ethyl]naphth-7-yl}-N-tetramethylene-methanesulphonamide Example 29: 2-{6-[2-(Dimethylamino)ethyl]naphth-2-yl}-N-methyl-methanesulphonamide

Step I: 6-Acetyl-2-bromomethylnaphthalene

The procedure is as in Step II of Example 1, replacing 1-acetyl-7-methylnaphthalene with 6-acetyl-2-methyl-naphthalene (Example 1, Step I).

The 6-acetyl-2-bromomethylnaphthalene is obtained in a yield of 24%.

Melting point: 80° C.

Infrared (KBr disk): 1690 cm$^{-1}$ $\nu$ C=O, 1360 cm

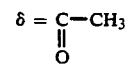

815 cm$^{-1}$ $\nu$ CH.

NMR (CDCl$_3$, TMS):

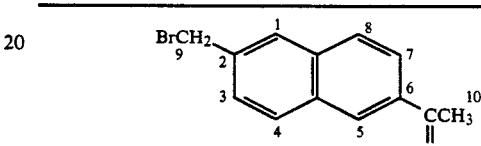

| Proton No. | 1 | 3 | 4 | 5 | 7 | 8 | 9 | 10 |
|---|---|---|---|---|---|---|---|---|
| δ (ppm) | 7.84 | 7.56 | 7.93 | 8.42 | 8.04 | 7.83 | 4.65 | 2.72 |

Step II: Sodium 2-(6-Acetylnaphth-2-yl)methanesulphonate

The procedure is as in Step III of Example 1, replacing 1-acetyl-7-bromomethylnaphthalene with 6-acetyl-2-bromomethylnaphthalene.

The sodium 2-(6-acetylnaphth-2-yl)methanesulphonate is obtained in a yield of 87%.

Melting point: >260° C.

Microanalysis: calculated C(52.08), H(4.20). found C(52.05), H(4.12).

Infrared (KBr disk): 3040–2900 cm$^{-1}$ $\nu$ CH (alkyl), 1620 cm$^{-1}$ $\nu$ C=O, 1620 cm$^{-1}$ $\nu$ C=C (aromatic), 1060 cm$^{-1}$ $\nu$ SO$_2$.

NMR (DMSO, d$_6$) δ (ppm):

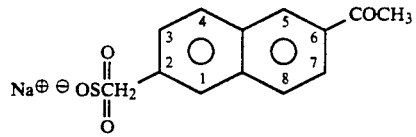

2.71 (s, 3H) CH$_3$, 3.84 (s, 2H) CH$_2$, 7.57–8.07 (unresolved peaks, 5H) H$_1$, H$_3$, H$_4$, H$_7$, H$_8$, 8.63 (1H) H$_5$.

Step III: 2-(6-Acetylnaphth-2-yl)methanesulphonic Acid Chloride

The procedure is as in Step IV of Example 1, replacing sodium 2-(1-acetylnaphth-7-yl)methanesulphonate with sodium 2-(6-acetylnaphth-2-yl)methanesulphonate.

The 2-(6-acetylnaphth-2-yl)methanesulphonic acid chloride is obtained in a yield of 96%.

Melting point: 105°–107° C.

Infrared (KBr disk): 3000–2900 cm$^{-1}$ $\nu$ CH (alkyl), 1670 cm$^{-1}$ $\nu$ C=O, 1620 cm$^{-1}$ $\nu$ C=C (aromatic), 1160 cm$^{-1}$ $\nu$ SO$_2$.

NMR (DMSO, d$_6$) δ (ppm):

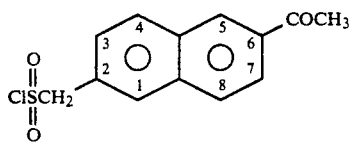

2.75 (s, 3H) CH₃, 5.07 (s, 2H) CH₂, 7.57–8.19 (unresolved peaks, 5H) H₁, H₃, H₄, H₇, H₈, 8.50 (H) H₅.

Step IV:
2-(6-Acetylnaphth-2-yl)-N-methyl-methanesulphonamide

The procedure is as in Step V of Example 1, replacing 2-(1-acetylnaphth-7-yl)methanesulphonic acid chloride with 2-(6-acetylnaphth-2-yl)methanesulphonic acid chloride.

The 2-(6-acetylnaphth-2-yl)-N-methyl-methanesulphonamide is obtained in a yield of 70%.

Melting point: 167°–169° C.

Microanalysis: calculated C(60.63), H(5.45), N(5.05). found C(61.05), H(5.54), N(4.97).

Infrared (KBr disk): 3230 cm⁻¹ ν NH, 3040–2800 cm⁻¹ ν CH (alkyl), 1660 cm⁻¹ ν C=O, 1625 cm⁻¹ ν C=C (aromatic), 1330 cm⁻¹ ν SO₂.

NMR (DMSO, d₆) δ (ppm):

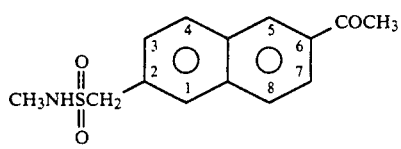

2.61 (d, 3H) CH₃NH (J CH₃NH=4.6 Hz, no coupling in D₂O), 2.67 (s, 3H)

4.57 (s, 2H) CH₂SO₂, 7.00 (q, 1H) NHCH₃ (J NHCH₃=4.6 Hz, no coupling in D₂O), 7.57–7.67 (dd, 1H), H₃ or H₇ (Jo=7.6 Hz, Jm=1.5 Hz), 8.00–8.19 (unresolved peaks, 4H), H₁, H₄, H₈, H₃ or H₇, 8.67 (1) H₅.

Step V:
2-(6-Bromoacetylnaphth-2-yl)-N-methyl-methanesulphonamide

The procedure is as in Step VI of Example 1, replacing the 2-(1-acetylnaphth-7-yl)-N-methyl-methanesulphonamide with 2-(6-acetylnaphth-2-yl)-N-methyl-methanesulphonamide.

The 2-(6-bromoacetylnaphth-2-yl)-N-methyl-methanesulphonamide is obtained in a yield of 87%.

Melting point: 208°–210° C.

Microanalysis: calculated C(46.03), H(4.13), N(3.83). found C(46.44), H(3.74), N(3.81).

Infrared (KBr disk): 3240 cm⁻¹ ν NH 3000–2800 cm⁻¹ ν CH (alkyl), 1685–1665 cm⁻¹ ν C=O, 1625 cm⁻ν C=C (aromatic), 1305 cm⁻¹ ν SO₂.

NMR (DMSO, d₆) δ (ppm):

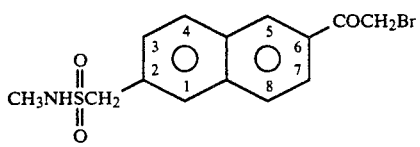

2.61 (d, 3H) CH₃NH (J CH₃NH=4.6 Hz, no coupling in D₂O), 4.57 (s, 2H) CH₂SO₂, 7.00 (q, 1H) CHCH₃ (J NHCH₃=4.6 Hz, no coupling in D₂O), 7.59–7.69 (dd, 1H), H₃ or H₇ (Jo=7.6 Hz, Jm=1.5 Hz), 8.00–8.19 (unresolved peaks, 4H), H₁, H₄, H₈, H₃ or H₇ 8.75 (H) H₅.

Step VI:
2-[6-(2-Bromoethyl)naphth-2-yl]-N-methyl-methanesulphonamide

The procedure is as in Step VII of Example 1, replacing the 2-(1-bromoacetylnaphth-7-yl)-N-methyl-methanesulphonamide with 2-(6-bromoacetylnaphth-2-yl)-N-methyl-methanesulphonamide.

The 2-[6-(2-bromoethyl)naphth-2-yl]-N-methyl-methanesulphonamide is obtained in a yield of 70%.

Melting point: 155°–157° C.

Microanalysis: calculated C(49.12), H(4.71), N(4.09). found C(49.66), H(4.70), N(4.42).

Infrared (KBr disk): 3265 cm⁻¹ ν NH, 1600 cm⁻¹ ν C=C (aromatic), 1310 cm⁻¹ ν SO₂.

NMR (DMSO, d₆) δ (ppm):

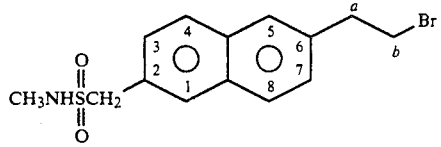

2.60 (d, 3H) CH₃NH (J CH₃NH=5.7 Hz, disappears in D₂O), 3.32 (t, 2H) Ha (Ja,b=7.1 Hz), 3.84 (t, 2H) Hb (Jb,a=7.1 Hz), 4.50 (s, 2H) CH₂SO₂, 6.84 (q, 1H) NHCH₃ (J NHCH₃=5.7 Hz, disappears in D₂O), 7.42–7.94 (unresolved peaks, 6H), H₁, H₃, H₄, H₅, H₇, H₈.

Step VII: 2-55 6-[2-(Dimethylamino)ethyl]naphth-2-yl}-N-methyl-methanesulphonamide The procedure is as in Step VIII of Example 1, replacing the 2-[1-(2-bromoethyl)naphth-7-yl]-N-methyl-methanesulphonamide with 2-[6-(2-bromoethyl)naphth-2-yl]-N-methyl-methanesulphonamide.

The 2-{6-[2-(dimethylamino)ethyl]naphth-2-yl}-N-methyl-methanesulphonamide is obtained in a yield of 38%.

Melting point: 177°–179° C.

Microanalysis: calculated C(2.71), H(7.23), N(9.14). found C(62.70), H(7.32), N(8.90).

Infrared (KBr disk): 3020–3040 cm⁻¹ ν NH (sulphonamide), 3950–2760 cm⁻¹ ν CH (alkyl), 1600 cm⁻¹ ν C=C (aromatic), 1320 cm⁻¹ ν SO₂.

NMR (DMSO, d₆) δ (ppm):

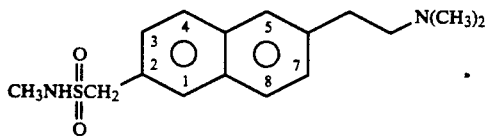

2.21 (s, 6H) N(CH$_3$)$_2$, 2.35–2.50 (m, 2H), H$_b$, 2.60 (d, 3H) CH$_3$NH (J CH$_3$NH=4.2 Hz, disappears in D$_2$O), 2.79–3.00 (m, 2H) Ha, 4.57 (S, 2H) CH$_2$SO$_2$, 6.91 (q, 1H), NHCH$_3$ (J NHCH$_3$=4.2 Hz, disappears in D$_2$O), 7.38–7.50 (dd, 2H) H$_3$ and H$_7$ (Jo=8.4 Hz, Jm=2.8 Hz), 7.71–7.87 (unresolved peaks, 4H) H$_1$, H$_4$, H$_5$, H$_8$.

EXAMPLES 30 to 37

By proceeding as in Examples 2 to 6, but replacing the 2-[1-(2-bromoethyl)naphth-7-yl]-N-methyl-methanesulphonamide with 2-[6-(2-bromoethyl)naphth-2-yl]-N-methyl-methanesulphonamide the following are obtained:

Example 30: 2-[6-(2-Aminoethyl)naphth-2-yl]-N-methyl-methanesulphonamide

Example 31: 2-[6-(2-Morpholinoethyl)naphth-2-yl]-N-methyl-methanesulphonamide

Example 32: 2-{6-[2-(3-Azabicyclo[3.3.0]oct-3-yl)-ethyl]naphth-2-yl}-N-methyl-methanesulphonamide Example 33: 2-[6-(2-Piperidinoethyl)naphth-2-yl]-N-methyl-methanesulphonamide Hydrochloride Example 34: 2-{6-[2-(4-Metatrifluoromethylphenylpiperazin-1-yl)ethyl]naphth-2-yl}-N-methyl-methanesulphonamide Hydrochloride Example 35: 2-{6-[2-(4-Paramethoxyphenylpiperazin-1-yl)-ethyl]naphth-2-yl}-N-methyl-methanesulphonamide Hydrochloride Example 36: 2-{6-[2-(4-(2,3,4-Trimethoxybenzylpiperazin-1-yl)ethyl]naphth-2-yl}-N-methyl-methanesulphonamide Hydrochloride Example 37: 2-55 6-[2-(4-Phenylhomopiperazin-1-yl)ethyl]naphth-2-yl}-N-methyl-methanesulphonamide Hydrochloride Example 38: 2-{6-[2-(4-Benzoylpiperazin-1-yl)ethyl]naphth-2-yl}-N-methyl-methanesulphonamide 2-{6-[2-(4-benzoylpiperazin-1-yl)ethyl]naphth-2-yl}-N-methyl-methanesulphonamide is obtained by proceeding as in Example 34 but replacing the 1-(meta-trifluoromethylphenyl)piperazine with 1-benzoylpiperazine.

By proceeding in the same manner there is obtained:

Example 39: 2-{1-[2-(4-Acetylpiperazin-1-yl)ethyl]naphth-7-yl}-N-methyl-methanesulphonamide

EXAMPLES 40 to 53

By proceeding as in Examples 12 to 23, but replacing the 2-[1-(2-bromoethyl)naphth-7-yl]-N-methyl-methanesulphonamide with 2-[6-bromoethylnaphth-2-yl]-N-methyl-methanesulphonamide the following are obtained:

Example 40: 2-{6-[2-(3-Azaspiro[5.5]undecan-3-yl)ethyl]naphth-2-yl}-N-methyl-methanesulphonamide Hydrochloride Example 41: 2-{6-[2-(3-Azabicyclo[3.2.2]nonan-3-yl)ethyl]naphth-2-yl}-N-methyl-methanesulphonamide Hydrochloride Example 42: 2-[6-(2-Pyrrolidinoethyl)naphth-2-yl]-N-methyl-methanesulphonamide Hydrochloride Example 43: 2-[6-(2-Thiomorpholinoethyl)naphth-2-yl]-N-methyl-methanesulphonamide Hydrochloride Example 44: 2-[6-(2-Hexamethyleneiminoethyl)naphth-2-yl]-N-methyl-methanesulphonamide Hydrochloride Example 45: 2-[6-(2-Heptamethyleneiminoethyl)-naphth-2-yl]-N-methyl-methanesulphonamide Hydrochloride Example 46: 2-{6-[2-(N,N-Dipropylamino)ethyl]-naphth-2-yl}-N-methyl-methanesulphonamide Hydrochloride Example 47: 2-{6-[2-(N-Benzyl-N-methylamino)ethyl]-naphth-2-yl}-N-methyl-methanesulphonamide Hydrochloride Example 48: 2-{6-[2-(N-Methyl-N-phenylamino)ethyl]-naphth-2-yl}-N-methyl-methanesulphonamide Hydrochloride Example 49: 2-{6-[2-(N-Cyclohexylamino)ethyl]-naphth-2-yl}-N-methyl-methanesulphonamide Hydrochloride Example 50: 2-{6-[2-(N-Methylamino)ethyl]naphth-2-yl}-N-methyl-methanesulphonamide Example 51: 2-{6-[2-(N-Methyl-N-ethylamino)ethyl]-naphth-2-yl}-N-methyl-methanesulphonamide Example 52: 2-{6-[2-(N-4-Fluorophenylamino)ethyl]-naphth-2-yl}-N-methyl-methanesulphonamide Hydrochloride Example 53: 2-{6-[2-(N-3,4-Dichlorophenylamino)ethyl]naphth-2-yl}-N-methyl-methanesulphonamide Hydrochloride Example 54: 2-{6-[2-(N-Allylamino)ethyl]naphth-2-yl}-N-methyl-methanesulphonamide 2-55 6-[2-(N-allylamino)ethyl]naphth-2-yl}-N-methyl-methanesulphonamide is obtained by proceeding as in Example 29 but replacing the dimethylamine with allylamine.

Example 55: 2-{6-[2-Dimethylamino)ethyl]naphth-2-yl}-N-benzyl-methanesulphonamide 2-{6-[2-(dimethylamino)ethyl]naphth-2-yl}-N-benzyl-methanesulphonamide is obtained by proceeding as in Example 24 but replacing the 2-[1-(2-bromoethyl)-naphth-7-yl]-N-benzyl-methanesulphonamide with 2-[6-(2-bromoethyl)naphth-2-yl]-N-benzyl-methanesulphonamide.

EXAMPLES 56 to 59

By proceeding as in Example 55, but replacing the 2-[6-(2-bromoethyl)naphth-2-yl]-N-benzyl-methanesulphonamide with:

6-(2-bromoethyl)-2-morpholinosulphonylmethyl-naphthalene, there is obtained:

Example 56: 6-[2-(Dimethylamino)ethyl]-2-(Morpholinosulphonylmethyl)naphthalene

2-[6-(2-bromoethyl)naphth-2-yl]-N,N-dimethylmethanesulphonamide, there is obtained:

Example 57: 2-{6-[2-(Dimethylamino)ethyl]naphth-2-yl}-N,N-dimethyl-methanesulphonamide 2-[6-(2-bromoethyl)naphth-2-yl]-N-cyclopentylmethanesulphonamide, there is obtained:

Example 58: 2-{6-[2-(Dimethylamino)ethyl]naphth-2-yl}-N-cyclopentyl-methanesulphonamide 2-[6-(2-bromoethyl)naphth-2-yl]-N-tetramethylenemethanesulphonamide, there is obtained:

Example 59: 2-{6-[2-(Dimethylamino)ethyl]naphth-2-yl}-N-tetramethylene-methanesulphonamide Example 60: 2-Δ7-[2-(Dimethylamino)ethyl]naphth-1-yl]-N-methyl-methanesulphonamide 2-{7-[2-(Dimethylamino)ethyl]naphth-1-yl}-N-methyl-methanesulphonamide is obtained by proceeding as in Example 1, but replacing the 1-acetyl-7-methylnaphthalene with 7-acetyl-1-methylnaphthalene (Bull. Soc. Chim. Fr. (1978) pp 104-108).

Infrared (KBr disk): 3030-3070 cm$^{-1}$ ν NH, 1600 cm$^{-1}$ ν C=C (aromatic), 1320 cm$^{-1}$ ν SO$_2$.

Example 61:
2-{1-[2-(Dimethylamino)ethyl]naphth-7-yl}-N-methylacetamide

The procedure is as for 2-{1-[2-(dimethylamino)ethyl]naphth-7-yl}-N-methyl-methanesulphonamide (Example 1), replacing the 2-(1-acetylnaphth-7-yl)methanesulphonic acid chloride in Step V with 2-(1-acetylnaphth-7-yl)acetic acid chloride.

2-{1-[2-(dimethylamino)ethyl]naphth-7-yl}-N-methyl-acetamide is obtained in a yield of 35%.

Melting point: 159°-163° C. (hydrochloride)

Infrared (KBr disk) (hydrochloride): 3330-3060 cm$^{-1}$ ν NH, 3030-2800cm$^{-1}$ ν CH, 2250-1700 cm$^{-1}$ ν NH$^+$ hydrochloride, 1670-1660 cm$^{-1}$ ν C=O amide.

NMR (DMSO, d$_6$) δ (ppm):

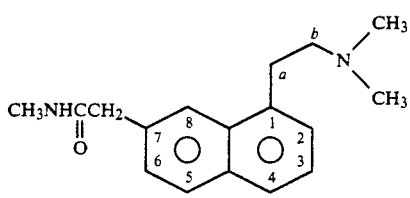

2.61 (m, 3H) CH$_3$NH, 2.86 (d, 6H) (CH$_3$)$_2$ N$^+$, 3.44 (m, 4H), Ha, Hb, 3.66 (s, 2H) CH$_2$CO, 6.63 (signal, 1H), NHCH$_3$ (disappears in D$_2$O), 7.38-7.94 (unresolved peaks, 5H), H$_2$, H$_3$, H$_4$, H$_5$, H$_6$, 8.22 (signal, 1H), H$_8$, 11.05 (signal, 1H), NH$^+$ (disappears in D$_2$O).

2-(1-acetylnaphth-7-yl)acetic acid chloride is obtained in conventional manner by treatment with 2-(1-acetylnaphth-7-yl)acetic acid thionyl chloride which is prepared in the following manner:

Step I: 2-(1-Acetylnaphth-7-yl)acetonitrile

Method A

Heat a suspension of sodium cyanide in 25 cm$^3$ of DMSO at 60° C. for 30 minutes, then progressively add 10 g of 1-acetyl-7-bromomethylnaphthalene.

Continue heating at 60° C. for 90 minutes, then cool and pour the reaction mixture into 300 cm$^3$ of water.

The precipitate which forms is isolated by filtration, washed with water, dried and then recrystallised from ethanol.

In that manner 2-(1-acetylnaphth-7-yl)acetonitrile is obtained in a yield of 96%.

Method B

Heat a mixture of 15 g of 1-acetyl-7-bromomethylnaphthalene and 3 g of sodium cyanide in 150 cm$^3$ of ethanol at reflux for 10 hours.

After cooling and concentrating to dryness, take up the reaction mixture in diluted sodium hydroxide solution, extract with ether and then concentrate to dryness.

In that manner 2-(1-acetylnaphth-7-yl)acetonitrile is obtained in a yield of approximately 50%.

Melting point: 88° C.

Infrared (KBr disk): 3100-2900 cm$^{-1}$ ν CH, 2240 cm$^{-1}$ ν C=N, 1660-1650 cm$^{-1}$ ν C=O, NMR (CDCl$_3$) δ (ppm):

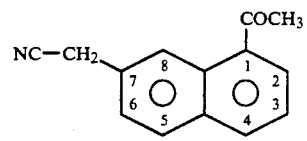

2.78 (s, 3H) CH$_3$, 3.92 (s, 2) CH$_2$, 7.42-8.07 (m, 5H) H$_2$, H$_3$, H$_4$, H$_5$, H$_6$, 8.78 (s, 1H) H$_8$.

Step II: 2-(1-Acetylnaphth-7-yl)Acetic Acid

Method A

Dissolve 3 g 2-(1-acetylnaphth-7-yl)acetonitrile in 10 cm$^3$ of acetic acid with the application of heat.

Add 40 cm$^3$ of concentrated hydrochloric acid then heat at reflux for 3 hours.

After cooling, the reaction mixture is poured into 200 cm$^3$ of water and the resulting precipitate is isolated by means of filtration, washed with water, dried and then recrystallised from ethanol at 95°.

In that manner, 2-(1-acetylnaphth-7-yl)acetic acid is obtained in a yield of 80%.

Method B

Heat at 100° C., for 48 hours, a mixture consisting of a solution of 15 g of 2-(1-acetylnaphth-7-yl)acetonitrile in 125 cm$^3$ of ethylene glycol monomethyl ether to which 0.5 mol of potassium hydroxide in 75 cm$^3$ of water has been added.

After cooling, the aqueous phase is washed with ether and then rendered acidic with 1N hydrochloric acid.

The acid which precipitates is isolated by means of filtration.

In that banner 2-(1-acetylnaphth-7-yl)acetic acid is obtained in a yield of 60%.

Melting point: 131°-132 ° C.

Infrared (KBr disk): 3100-2700 cm$^{-1}$ ν OH, 1710-1700 cm$^{-1}$ ν C=O (acid), 1660 cm$^{-1}$ ν C=O (ketone).

NMR (CDCl$_3$) δ (ppm):

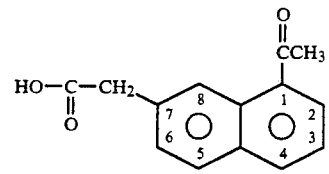

2.76 (s, 3H) CH$_3$, 3.88 (s, 2H) CH$_2$, 6.00 (s, 1H) OH (exchangeable in D$_2$O), 7.38-8.00 (m, 5H), H$_2$, H$_3$, H$_4$, H$_5$, H$_6$, 8.69 (s, 1H), H$_8$.

EXAMPLE 62

2-{6-[2-(Dimethylamino)ethyl]naphth-2-yl}-N-methylacetamide

The procedure is as in Example 61, replacing the 2-(1-acetylnaphth-7-yl)acetic acid chloride with 2-(6-acetylnaphth-2-yl)acetic acid chloride which has been obtained in the sake manner from 6-acetyl-2-bromomethylnaphthalene.

EXAMPLE 63

Pharmaceutical Compositions

Tablets each containing 5 mg of 2-{1-[2-(dimethylamino)ethyl]naphth-7-yl}-N-methanesulphonamide

| Formulation for preparing 1000 tablets | |
|---|---|
| 2-{1-[2-(dimethylamino)ethyl]naphth-7-yl}-N-methyl-methanesulphonamide | 5 g |
| wheat starch | 20 g |
| corn starch | 20 g |
| lactose | 70 g |
| magnesium stearate | 1 g |
| silica | 1 g |
| hydroxypropylcellulose | 2 g |

Pharmacological Study of the Compounds of the Invention

EXAMPLE A

In Vitro Determination of the Affinity for Serotoninergic Receptors

The in vitro affinity tests of the compounds of the invention for the receptors 5-$HT_1A$, 5-$HT_1C$, 5-$HT_1D$, 5-$HT_2$, 5-$HT_3$, $D_1$, $D_2$ $\alpha_1$, $\alpha_2$ were carried out according to conventional methods by displacement of a reference radioligand.

| RECEPTOR | RADIOLIGAND | TISSUE USED |
|---|---|---|
| 5-$HT_1A$ | 8-OH DPAT | hippocampus |
| 5-$HT_1C$ | N-methyl mesulergine | frontal cortex, hippocampus |
| 5-$HT_1D$ | 5-OH tryptamine | cortex + striatum + GP |
| 5-$HT_2$ | amino iodo ketanserin | frontal cortex |
| 5-$HT_3$ | BRL 43694 | Area postrema NTS |

The results of these binding studies show that the compounds of the invention exhibit a marked affinity for serotoninergic receptors associated with a pronounced selectivity for 5-$HT_1D$ receptors.

That selectivity for 5-$HT_1D$ receptors is also very significant (at least a factor of 100) in relation to the dopaminergic receptors $D_1$, $D_2$ and the adrenergic receptors $\alpha_1$, $\alpha_2$.

2-{1-[2-(dimethylamino)ethyl]naphth-7-yl}-N-methyl-methanesulphonamide, for example, has an affinity of the order of $10^{-7}$M for 5-$HT_1D$ receptors whilst its affinity for the other serotoninergic receptors is from $10^{-6}$M to $10^{-5}$M and for $D_1$, $D_2$, $\alpha_1$ and $\alpha_2$ receptors is less than $10^{-5}$M.

EXAMPLE B

Acute Toxicity Study

The acute toxicity "per os" of the compounds of the invention was evaluated after oral administration of the test compounds to groups of 10 SWISS mice (average weight 22 g).

The animals are observed at regular intervals during the course of the first day, and daily for the two weeks following treatment. The $LD_{50}$ (dose that causes the death of 50% of the animals) was evaluated.

For most of the test compounds, the $LD_{50}$ is greater than 1 g $kg^{-1}$, which indicates a weak acute toxicity "per os".

EXAMPLE C

In Vitro Demonstration of a Vasoconstrictive Activity in the Basilar Artery of Dogs Experiments are carried out on annular sections of the basilar artery of dogs from which the endothelium has been removed and which are placed in an organ chamber enabling the measurement of isometric contractions in the presence or absence of ketanserin.

The studies carried out demonstrate that the compounds of the invention, like serotonin, are capable of inducing contractions in arterial sections. The fact that those contractions are not antagonised by ketanserin shows that the contractions are not mediated by the 5-$HT_2$ receptors.

2-{1-[2-(dimethylamino)ethyl]naphth-7-yl}-N-methyl-methanesulphonamide, for example, has an $EC_{50}$ of the order of $10^{-6}$M in that test.

The same compound with the same doses does not show any significant effect on annular sections of the coronary artery or on sections of the saphenous vein.

We claim:

1. A compound selected from those of the formula (I):

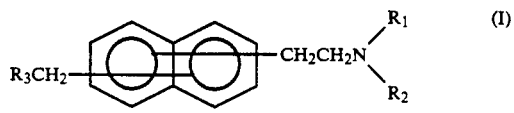

it being possible for each of the two substituents, independently of the other, to be located on either one of the two naphthalene rings, and wherein $R_1$ and $R_2$, which are the same different, each represents, independently of the other, a radical selected from:
hydrogen,
straight-chain or branched alkyl having 1 to 6 carbon atoms, inclusive,
cycloalkyl, having 3 to 7 carbon atoms, inclusive, or cycloalkyl(C1-C4)alkyl,
straight-chain or branched alkyl having 2 to 6 carbon atoms inclusive,
optionally substituted aryl,
and optionally substituted aralkyl of which the alkyl chain has 1 to 3 carbon atoms, inclusive, $R_3$ represents:

a group 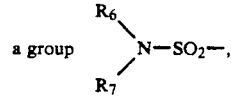

wherein $R_6$ and $R_7$, which are the same or different, have the same definition as $R_1$ and $R_2$,
an optical isomer therefore,
and an addition salt with a pharmaceutically-acceptable mineral or organic acid;
"aryl" meaning a group selected from phenyl, naphthyl;
the expression "optionally substituted meaning that the aromatic nucleus or nuclei may be substituted by one or more radicals selected from hydroxy, halogen, trifluoromethyl, nitro, straight-chain or branched alkyl having 1 to 6 carbon atoms, inclusive, and straight-chain or branched alkoxy having 1 to 6 carbon atoms, inclusive.

2. A compound according to claim 1 selected from those of the formula (I$_A$):

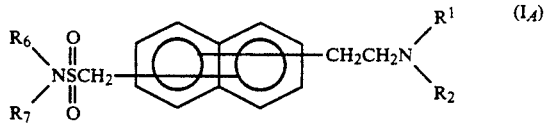

wherein, it being possible for each of the two substituents, independently of the other, to be located on either one of the two naphthalene rings, R$_1$, R$_2$, R$_6$ and R$_7$ are as defined in claim 1, an optical isomer thereof, and an addition salt with a pharmaceutically-acceptable mineral or organic acid.

3. A compound according to claim 1 in which the two substituents are located at apices 1 and 7 of the naphthalene nucleus and which corresponds to a compound selected from those of the following formula:

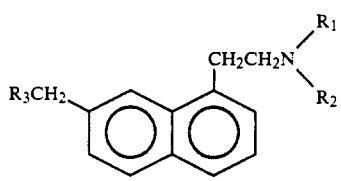

wherein R$_1$, R$_2$, R$_3$ are as defined in claim 1, an optical isomer thereof, and an addition salt with a pharmaceutically-acceptable mineral or organic acid.

4. A compound according to claim 1 in which the two substituents are located at apices 1 and 7 of the naphthalene nucleus and which corresponds to a compound selected from those of the following formula:

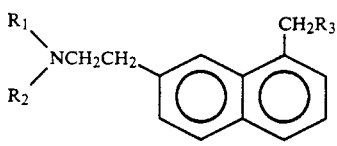

wherein R$_1$, R$_2$, R$_3$ are as defined in claim 1, an optical isomer thereof, and an addition salt with a pharmaceutically-acceptable mineral or organic acid.

5. A compound according to claim 1, which is selected from 2-{1-[2-(dimethylamino)ethyl]naphth-7-yl}-N-methyl-methanesulphonamide of which the formula is shown below, and an addition salt thereof with a pharmaceutically-acceptable mineral or organic acid,

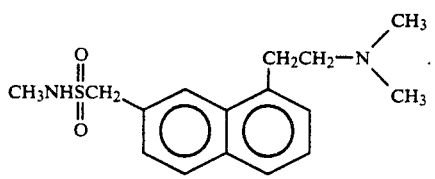

6. A compound according to claim 1, which is selected from 2-{7-[2-(dimethylamino)ethyl]naphth-1-yl}-N-methyl-methanesulphonamide of which the formula is shown below, and an addition salt thereof with a pharmaceutically-acceptable mineral or organic acid,

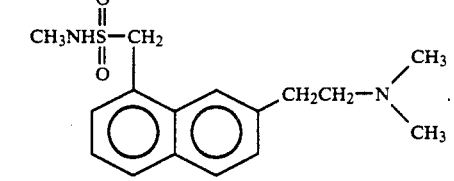

7. A compound according to claim 1, which is selected from 2-{1-[2-(N-methyl-N-ethylamino)ethyl]-naphth-7-yl}-N-methyl-methanesulphonamide of which the formula is shown below, and an addition salt thereof with a pharmaceutically-acceptable mineral or organic acid,

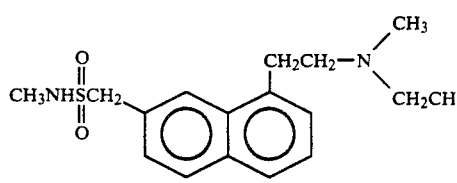

8. A compound according to claim 1, which is selected from 2-{1-[2-(dimethylamino)ethyl]naphth-7-yl}-N-methyl-methanesulphonamide of which the formula is shown below, and an addition salt thereof with a pharmaceutically-acceptable mineral or organic acid,

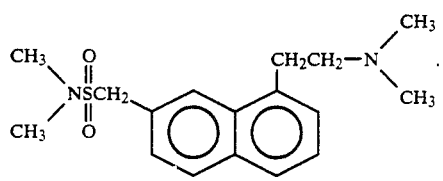

9. A compound according to claim 1, which is selected from 2-{1-[2-(N-methylamino)ethyl]naphth-7-yl}-N-methyl-methanesulphonamide of which the formula is shown below, and an addition salt thereof with a pharmaceutically-acceptable mineral or organic acid,

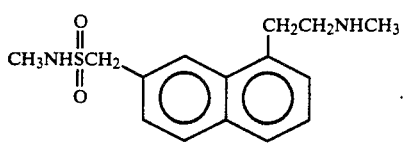

10. A pharmaceutical composition useful in treating a disorder due to vasodilatation of the vascular system, comprising as active principle an effective amount of a compound as claimed in claim 1, in combination with a pharmaceutically-acceptable carrier or diluent.

11. A method of treating a living mammal afflicted with a disorder due to vasodilatation of the vascular system, comprising the step of administering to the said living mammal an amount of a compound as claimed in claim 1, which is effective for alleviation of said disorder.

* * * * *

UNITED STATES PATENT AND TRADEMARK OFFICE
CERTIFICATE OF CORRECTION

PATENT NO. : 5,332,759

DATED : July 26, 1994

INVENTOR(S) : Patrick Depreux, Daniel Lesieur, Habib Abdellaoui, Bèatrice Guardiola, Gèrard Adam, Pierre Renard, Bruno Pfeiffer It is certified that error appears in the above-indentified patent and that said Letters Patent is hereby corrected as shown below:

```
Column  6, line 23; "DMG" should read -- DMF --

Column  7, line 27; "-2" should read -- -2- --
Column  7, line 61; move "1360 cm" down to next line to go with
        the formula.
Column  8, line 18; "with sti" should read -- with stirring --
Column  8, line 53; "oxy" should read -- oxychloride --

Column 11, line 29; "D₂)," should read -- D₂O), --
Column 12, line 30; "cm³¹¹" should read -- cm⁻¹ --

Column 15, line 22; "N-methanesulphonamide" should read
        -- N-methyl-methanesulphonamide --
Column 19, line 10; "8.50(H)" should read -- 8.50(1H) --
Column 19, line 48; "8.67(1)" should read -- 8.67(1H) --
Column 19, line 64; "C(46.44)" should read -- C(46.34) --
Column 19, line 67; "cm-v C=C" should read -- cm⁻¹v C=C --
Column 20, line 11; "CHCH₃" should read -- NHCH₃ --
Column 20, line 14; "8.75(H)" should read -- 8.75(1H) --
Column 20, line 50; "Step VII: 2-55" should read
        -- Step VII: --
Column 20, line 51; "6-[2-" should read -- 2-{6-[2- --
Column 20, line 62; "C(.71)," should read -- C(62.71), --
Column 21, line  1; (the formula) insert a -- 6 -- in the
        corner, between "5" and "7"
Column 21, line 39; "2-55 6-[2-" should read -- 2-{6-[2- --
Column 22, line  1; "44:" should read -- Example 44: --
Column 22, line 30; "2-55 6-[2-" should read
        -- 2-{6-[2- --
```

UNITED STATES PATENT AND TRADEMARK OFFICE
CERTIFICATE OF CORRECTION

PATENT NO. : 5,332,759

DATED : July 26, 1994

INVENTOR(S) : Patrick Depreux, Daniel Lesieur, Habib Abdellaoui, Bèatrice Guardiola, Gèrard Adam, Pierre Renard, Bruno Pfeiffer It is certified that error appears in the above-indentified patent and that said Letters Patent is hereby corrected as shown below:

Column 22, line 64; "2-Δ7-[2-" should read -- 2-{7-[2- --
Column 23, line 32; delete the commas after "4H)" and "1H)"
Column 23, line 34; delete the commas after "5H)" and "1H)"
Column 23, line 35; delete the comma after "1H)"
Column 24, line 9; (line under the drawing) "(s,2)" should read -- (s,2H) --
Column 24, line 67; "sake" should read -- same --
Column 25, line 3; "-N-methanesulphonamide" should read -- -N-methyl-methanesulphonamide --
Column 26, line 35; insert the word -- or -- between "same" and "different"
Column 26, line 44; "alkyl" should read -- alkenyl --
Column 26, line 59; "therefore" should read -- thereof --

Column 26, line 64; insert -- " -- after the word "substituted"
Column 28, line 29; "N-methyl-" should read -- -N,N-dimethyl- --

Signed and Sealed this

Seventeenth Day of January, 1995

Attest:

BRUCE LEHMAN

Attesting Officer

Commissioner of Patents and Trademarks